(12) United States Patent
Salgo et al.

(10) Patent No.: US 8,287,457 B2
(45) Date of Patent: Oct. 16, 2012

(54) 3D ECHOCARDIOGRAPHIC SHAPE ANALYSIS

(75) Inventors: Ivan Salgo, Pelham, MA (US); William B. Ackerman, North Billerica, MA (US)

(73) Assignee: Koninklijke Philips Electronics N.V, Eindhoven (NL)

( * ) Notice: Subject to any disclaimer, the term of this patent is extended or adjusted under 35 U.S.C. 154(b) by 945 days.

(21) Appl. No.: 12/301,495

(22) PCT Filed: May 17, 2007

(86) PCT No.: PCT/IB2007/051896
§ 371 (c)(1),
(2), (4) Date: Nov. 19, 2008

(87) PCT Pub. No.: WO2007/138523
PCT Pub. Date: Dec. 6, 2007

(65) Prior Publication Data
US 2010/0056915 A1 Mar. 4, 2010

Related U.S. Application Data

(60) Provisional application No. 60/803,145, filed on May 25, 2006, provisional application No. 60/803,274, filed on May 26, 2006, provisional application No. 60/864,273, filed on Nov. 3, 2006.

(51) Int. Cl.
*A61B 8/00* (2006.01)
(52) U.S. Cl. ........................................ 600/437; 382/128
(58) Field of Classification Search .......... 600/437–469; 382/128–133
See application file for complete search history.

(56) References Cited

U.S. PATENT DOCUMENTS

| | | | | |
|---|---|---|---|---|
| 5,435,310 A | * | 7/1995 | Sheehan et al. | 600/416 |
| 5,515,856 A | * | 5/1996 | Olstad et al. | 600/440 |
| 6,187,032 B1 | * | 2/2001 | Ohyu et al. | 600/409 |
| RE37,088 E | * | 3/2001 | Olstad et al. | 600/440 |
| 6,447,454 B1 | * | 9/2002 | Chenal et al. | 600/449 |
| 7,043,063 B1 | * | 5/2006 | Noble et al. | 382/128 |
| 2002/0072672 A1 | * | 6/2002 | Roundhill et al. | 600/450 |
| 2002/0072674 A1 | * | 6/2002 | Criton et al. | 600/454 |
| 2003/0171668 A1 | * | 9/2003 | Tsujino et al. | 600/407 |
| 2006/0122512 A1 | * | 6/2006 | Abe | 600/454 |
| 2009/0136109 A1 | * | 5/2009 | Salgo et al. | 382/131 |
| 2009/0161938 A1 | * | 6/2009 | Shekhar et al. | 382/131 |

OTHER PUBLICATIONS

Deformable Models with Parameter Functions for Cardiac Motion Analysis from Tagged MRI Data to Park et al. dated 1996.*
Scowen, B.C., et al., "Quantative 3D Modelling of the Left Ventrical From Ultrasound Images," Euromicro Conference, 2000. Proceedings of The 26th Sep. 5-7, 2000, Los Alamitos, CA, USA, IEEE Comput. Soc., US, vol. 2, Sep. 5, 2000, pp. 432-439, XP010514276.
Moses, D. A., et al., "Quantification of the Curvature and Shape of the Interventricular Septum," Magnetic Resonance in Medicine, Wiley USA, vol. 52, No. 1, Jul. 2004, pp. 154-163, XP002451153.

* cited by examiner

*Primary Examiner* — Sanjay Cattungal
(74) *Attorney, Agent, or Firm* — W. Brinton Yorks, Jr.

(57) ABSTRACT

An ultrasound system and method are described for assessing cardiac performance which is particularly useful for diagnosing heart remodeling. A 3D data set of a surface of the heart is acquired and the principal curvatures determined at one or more points of the surface. A curvature metric is produced which is the difference of the two principal curvatures at each point. Metrics produced from the heart surface acquired at systole have been found to correlate strongly with ejection fraction.

15 Claims, 4 Drawing Sheets

3D ECHOCARDIOGRAPHIC SHAPE ANALYSIS

This application claims the benefit of U.S. provisional patent application Ser. Nos. 60/803,145, filed May 25, 2006, 60/803,274, filed May 26, 2006, and 60/864,273, filed Nov. 3, 2006.

The evaluation of left ventricular (LV) remodeling is an essential process in assessing post myocardial infarction or patients undergoing cardiac resynchronization therapy (CRT). As the disease of a heart progresses, the heart muscle attempts to adapt to its changing condition. One manifestation of this adaptation is a change in the shape of the heart from its normal, roughly elongate shape to a more spherical shape. As the heart fails, the heart tries to maintain its pumping function by evolving to a spherical shape and redistributing its contraction function. Prior attempts to examine this change in shape, referred to as remodeling, have focused on characterizing the sphericity of the heart. Classic parameters used in this regard have been LV volumes as measured by 2D echo (with geometric assumptions) and end-diastolic sphericity. These traditional techniques do not, however, quantify local shape changes. Detecting and quantifying the shape of the heart in localized regions can lead to a detection of heart disease earlier in the disease progression, enabling early treatment designed to halt or reverse the effects of the heart disease. Accordingly it is desirable to be able to detect and quantify the shape of the heart in local regions as well as that of the entire heart.

In accordance with the principles of the present invention an ultrasound system and method are described which produce a metric that quantifies LV apical dilatation using methods of differential geometry on 3D (three dimensional) echocardiographic data without any geometric assumptions. In a particular example described below the metric is based upon the principal curvatures at one or more points on the endocardial wall of the heart. The metric can be calculated in real time over the entire cardiac cycle. A metric can be produced which focuses on the apical region of the heart, which is known to be the first region of the heart to show a shape change. It is believed that this apical shape index correlates directly with LV systolic function as measured by ejection fraction (EF).

Figure 1:
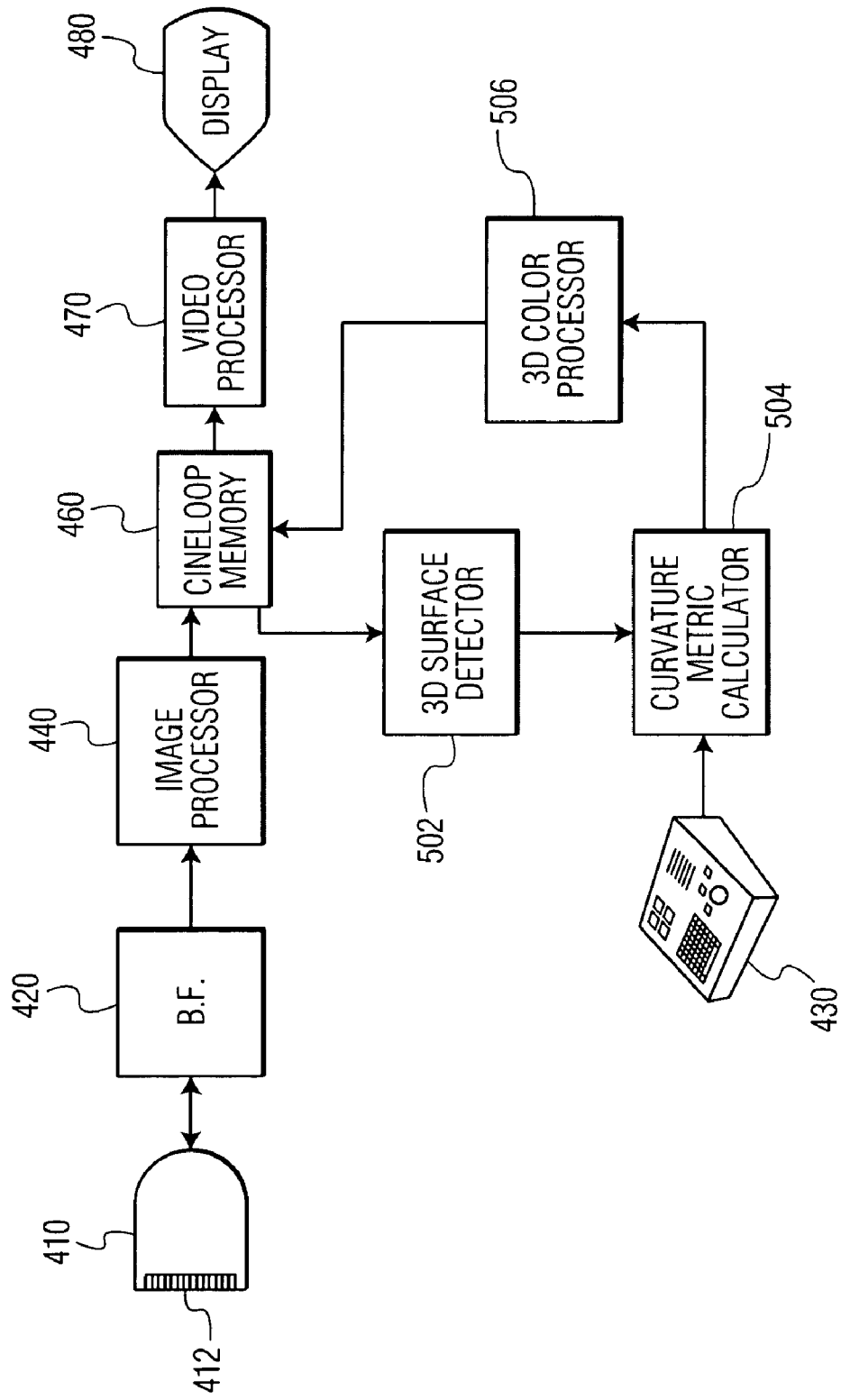
FIG. 1 illustrates in block diagram form an ultrasound system constructed in accordance with the principles of the present invention.

Referring first to FIG. 1, an ultrasound system constructed in accordance with the present invention is shown in block diagram form. A probe or scanhead 410 which includes a two dimensional (2D) array 412 of transducer elements transmits ultrasonic waves and receives ultrasonic echo signals. This transmission and reception is performed under control of a beamformer 420 which processes received echo signals to form coherent beams of echo signals from the anatomy being scanned. The echo information is coupled to an image processor 440 which processes the echo information into image signals as by amplitude detection, for instance. For B mode imaging of tissue structure the echo signals are image processed by amplitude detection and scan converted into the desired image format for display. The images pass through a Cineloop® memory 460 from which they may be coupled directly to a video processor 470 for display on an image display 480. The Cineloop memory can also be operated to capture a sequence of recently acquired real time images for storage and later inspection and diagnosis. The sequence of captured images, referred to as a "loop" of images, can extend over one or more heart cycles.

In accordance with the principles of the present invention the images are applied to a 3D surface detector 502. A suitable 3D surface detector is that described in U.S. patent application Ser. No. 60/784,194, filed Mar. 20, 2006, the contents of which are incorporated herein by reference. This 3D surface detector operates by detecting a tissue boundary in a three dimensional image of the heart by a semi-automated technique. Alternatively, a fully automated border detection technique can be used as described in U.S. Pat. No. 6,447,453 (Chenal et al.) In the case of the heart, the tissue boundary so defined can be the endocardium, the epicardium, or an artificially defined surface. For example the mid-point between the epi- and endo-cardial walls can be defined from the epicardial and endocardial data as an artificially defined "surface" inside the myocardium.

The 3D surface data so defined is coupled to a curvature metric calculator 504. The curvature metric calculator utilizes the 3D surface data to produce one or more metrics of the curvature of the surface as described more fully below. A user interface 430 is coupled to the curvature metric calculator to enable the ultrasound system user to delineate the region or regions where such metrics are to be calculated. The region can comprise the entire surface characterized by a single metric to hundreds or thousands of points over the surface where separate metrics are calculated as described more fully below. These metrics and the 3D surface data are coupled to a 3D color processor, which color-encodes the 3D surface in accordance with the calculated metrics to produce a subjective image of the metric data. For a monochrome image the metrics may be encoded in grayscale values. The subjective and objective metric information is coupled back to the Cineloop memory 460 from which it is processed by the by the video processor 470 for viewing on the display 480.

Figure 2A:
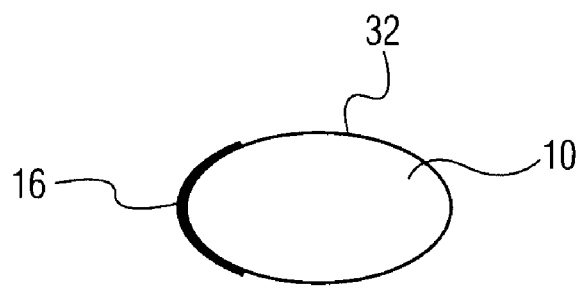
FIGS. 2a-2d illustrate the concept of principal curvatures of a surface.
Figure 2B:
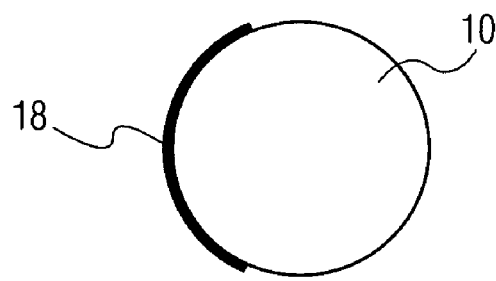

In a constructed implementation the curvatures used to compute the metric were the principal curvatures at the selected points on the 3D surface of the heart. The principal curvatures at a point on a surface are the curves of the surface passing through the point which exhibit the greatest and the least amount of curvature. It can be mathematically shown that for any surface these curves are orthogonal to each other. FIGS. 2a-2d illustrate this concept. FIGS. 2a and 2b are cross-sectional views of a piece 10 of the familiar M&M® chocolate candy. The cut plane of the view of FIG. 2a is vertically through the center of the piece of candy. Since an M&M is an oblate spheroid, this cut plane is generally oval as shown in FIG. 2a. The cut plane of the view of FIG. 2b is horizontally through the center of the piece of candy and is circular.

Figure 2C:

Imagine now any two curvatures on the top of the piece 10 of candy which pass through the point 32 on the top center of the M&M. Since the surface of the piece 10 of candy is symmetrical about the top center point, all of the curves passing through the center point are identical; they are all principal curvatures and any two of them which are orthogonal to each other can be taken as the two principal curvatures at this point 32. FIG. 2c illustrates these curves 12 and 14, which are seen to be the same.

Now suppose a coefficient is assigned to represent the curvature of each of these curves. The coefficients range from a large number for the tightest possible curve (greatest amount of curvature) to a small number for a curve with the least amount of curvature. A straight line might have a coefficient of zero, for instance. Since the curvatures of principal curves 12 and 14 are the same, their coefficients will be the same on any scale of coefficient values. We now calculate a metric equal to the difference of the curvature coefficients of the two principal curves. With the coefficients being equal, the difference of the two values will be zero. The metric $K_{Diff}$ is thus $$K_{Diff} = K_{max} - K_{min} \qquad (1)$$

By subtracting the smaller principal curvature from the larger, the value of $K_{Diff}$ will always be positive. Alternatively the absolute value of any order of subtraction can be used.

Figure 2D:
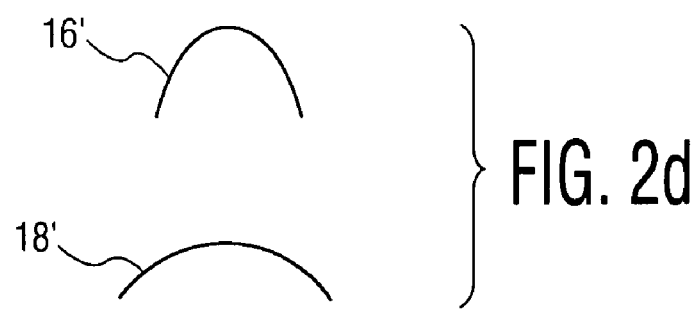

Now consider the case of a point on the side of the M&M designated by 16 and 18 in FIGS. 2a and 2b. At this point a vertical curve has a very tight curvature as shown by the darkened curve about point 16, but a much lesser curvature in the orthogonal plane of the darkened curve shown in FIG. 2b about point 18. These two curves are the principal curvatures at this side point of the M&M. The two orthogonal curves can be rotated together about the point 16,18 but in no other orientation is there a curve as tight as the curve in FIG. 2a or as shallow as the curve in FIG. 2b. These two principal curves 16' and 18' are shown in FIG. 2d.

When coefficients of curvature are assigned to these two curves on the same scale used for curves 12 and 14, the coefficient for curve 16' will be very large (much curvature) and the coefficient for curve 18' will be much smaller (much less curvature). When a difference metric is computed of this set of coefficients using equation (1), a relatively large number results. The difference between the two metrics computed for the M&M show that the surface curvatures at the side of the M&M have a large difference, whereas the difference at the top center of the M&M is zero. It is this concept which is used for the metric values of the illustrated example of the present invention.

Other combinations of the principal curvature coefficients can be used to define the metric, such as a sum, product, or quotient of the curvatures. However the difference is a preferred metric for its ability to best accentuate the spherical shape or pointed shape at and around the apex of the heart.

Figure 3A:
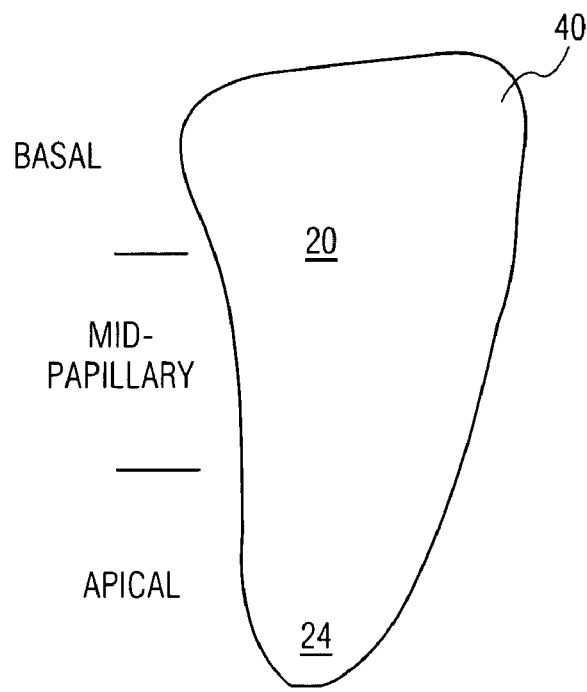
FIGS. 3a and 3b illustrate examples of surfaces of a normal and diseased heart.
Figure 3B:
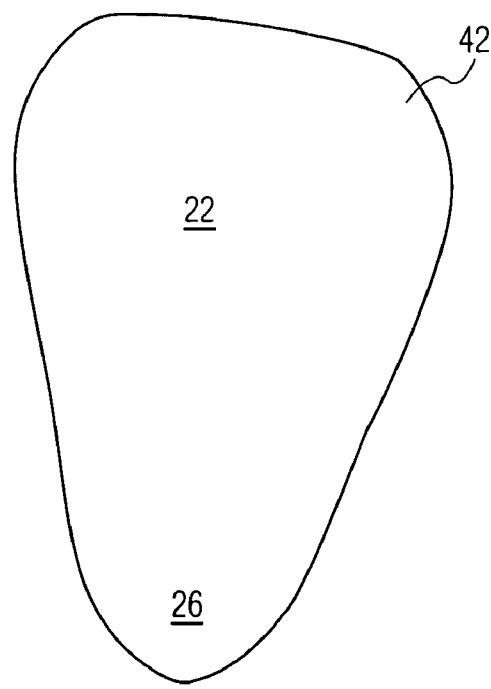

FIGS. 3a and 3b illustrate three dimensional heart surfaces 40,42 of a normal and dilated (more spherical) heart, respectively. To give the viewer a subjective sense of the metric values and their distribution over the heart surface 40 and 42, the range of metric values is used to select colors or hues from a color or hue range. This can be done by a lookup table, for instance. The drawings show the metric values in grayscale representation. In a constructed embodiment the colors ranged from yellow for areas with low metrics (little curvature) to red for areas with large metrics (considerable curvature), an example of the latter being at the apex of the normal heart shape 40.

As previously mentioned, the user interface 430 provides a means for the user to select points or regions of the surface where the metrics will be produced and/or over which metric values will be combined or averaged or a standard deviation calculated. Clinically, the heart is divided into basal, mid-papillary, and apical regions as shown adjacent to FIG. 3a. The user may decide to compute and analyze curvature metrics over only the apical region, for instance. Another possibility is for the user to designate specific points at which to compare curvature, such as point 24 near the apex and point 20 in the basal or mid-papillary region. The principal curvatures at point 24 would be considerably different as exemplified by the curves of FIG. 2d, whereas the principal curvatures at point 20 closer to the mitral valve at the top of the shape would be more similar, closer to the matched pair of FIG. 2c. The curvature metrics would differ correspondingly.

When metrics are computed at similar points 26 and 22 of the dilated heart 42, a different comparison is obtained. The metric at point 26 will be indicative of less curvature than that at point 24 of the normal heart, and the metric at point 22 will likewise indicate less curvature than similar point 20 of the normal heart. Thus, the curvature metrics are representative of the disease progression of the heart.

Figure 4:
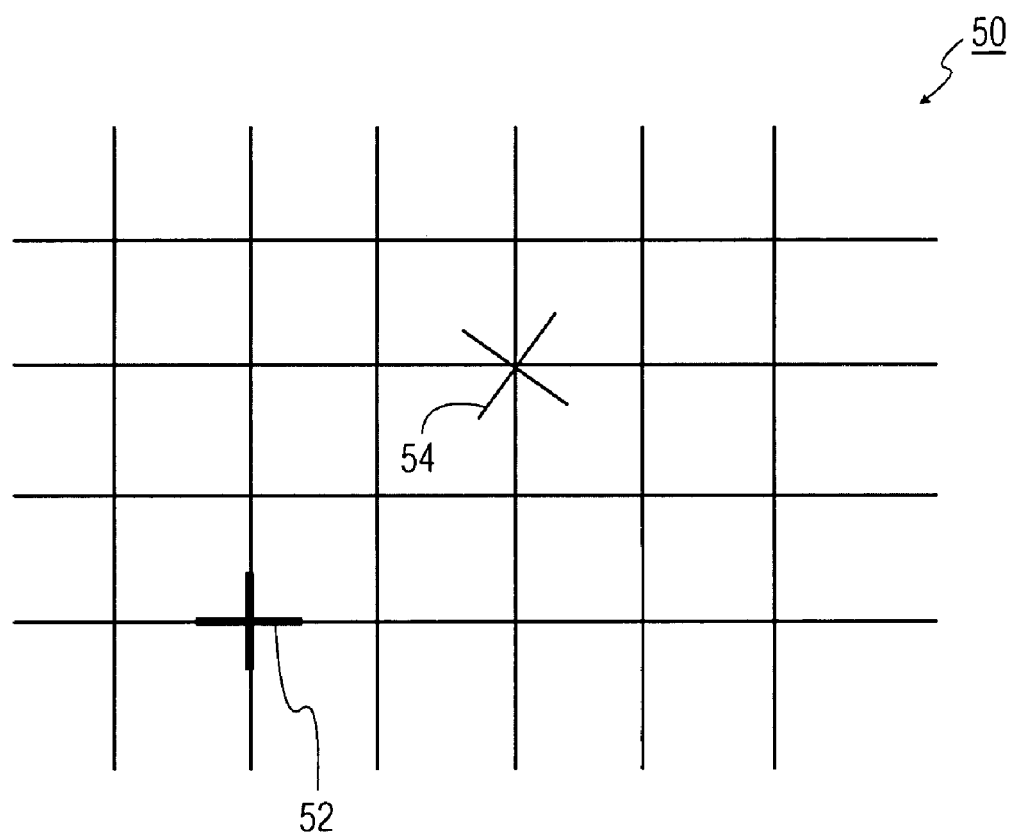
FIG. 4 illustrates one technique for locating points at which principal curvatures are determined.

As previously mentioned the metrics can be calculated over the full 3D surface if desired. In a constructed embodiment metrics are calculated at the intersection points of a mathematical pattern of grid lines 50 "wrapped" about the heart surface, as shown in FIG. 4. The grid lines 50 may be of any desired density. In the constructed embodiment a very high grid density was used. Metrics were then computed at every point of intersection of two grid lines. The two principal curvature curves shown at grid line intersection 52 are seen to be aligned with the grid lines, whereas the two principal curvature curves shown at grid line intersection 54 are not aligned with the grid lines. To produce the subjective 3D images of curvature metrics of FIGS. 3a and 3b grid lines were used which covered the entire heart surface at a very high density. The metric computed for each grid line intersection was converted to a corresponding color of the chosen color scale and displayed. The color scale may be chosen and adjusted by the user by means of the user interface 430.

Alternatively or in addition to producing metrics at each of a multitude of points over the entire heart surface, metrics can be calculated for smaller regions. All of the metrics of the apical region can be summed and/or averaged to produce one representative metric of curvature for the apical region, for instance. Other user-defined regions of a few square millimeters can be used. A metric can be computed for each of the seventeen AHA heart wall segments for example. One metric can be compiled from all of the individual metrics calculated to present the user with a single metric representative of heart curvature.

Other metrics comparing curvatures are also useful to analyze and represent cardiac performance, including the mean curvature at a point ((max+min)/2), Gaussian (max*min), longitudinal curvatures, circumferential curvatures, and the standard deviation of curvature, which is an indicator of the uniformity or sphericity of the LV.

The systolic apical shape index described above has been found to correlate strongly with ejection fraction (r=0.858, p<0.0005). The same shape index computed at diastole was found to correlate poorly (r=0.449, p<0.05) with ejection fraction. Thus, embodiments of the present invention which use systolic image data are believed to be more diagnostically useful. It is further believed that systolic apical shape is an important stratification parameter in assessing LV remodeling and is potentially useful in following patients post infarction and those undergoing CRT.

What is claimed is:

1. An ultrasound system for assessing cardiac performance comprising:
   a 3D surface processor responsive to 3D heart data which operates to delineate a three dimensional surface of the heart;
   a curvature processor responsive to the delineated heart surface which operates to produce curve representations at one or more points of the surface; and
   a curvature metric processor responsive to the curve representations for producing one or more metrics representing heart curvature, wherein the curvature processor further operates to produce coefficients representative of the principal curvatures at one or more points of the surface, and wherein the curvature metric processor produces a metric representative of the difference of principal curvature coefficients.

2. The ultrasound system of claim 1, further comprising a display which operates to display quantified curvature metrics.

3. An ultrasound system for assessing cardiac performance comprising:
   a 3D surface processor responsive to 3D heart data which operates to delineate a three dimensional surface of the heart;
   a curvature processor responsive to the delineated heart surface which operates to produce curve representations at one or more points of the surface; and
   a curvature metric processor responsive to the curve representations for producing one or more metrics representing heart curvature,
   wherein the curvature processor further operates to produce coefficients representative of the principal curvatures at one or more points of the surface, and
   wherein the curvature metric processor produces a metric representative of one or more of the mean, Gaussian, longitudinal, or circumferential curvature, or the standard deviation of curvature.

4. The ultrasound system of claim 3, wherein the curvature metric processor produces a metric representative of the curvature of the entire surface.

5. The ultrasound system of claim 3, wherein the curvature metric processor produces a metric representative of the curvature of a region of the surface.

6. The ultrasound system of claim 5, wherein the region comprises an area of a few square millimeters of the surface.

7. The ultrasound system of claim 5, wherein the region comprises an area corresponding to an AHA heart wall segment.

8. The ultrasound system of claim 5, wherein the curvature metric processor produces metrics at a plurality of points distributed over the entire surface.

9. The ultrasound system of claim 8, further comprising a metric processor responsive to metrics at a plurality of points on the surface which operates to produce an image of the surface with the metrics subjectively displayed.

10. The ultrasound system of claim 9, wherein the metrics are displayed by colors.

11. A method for assessing cardiac performance comprising:
    acquiring a three dimensional representation of a heart surface;
    computing the surface curvature at one or more points of the heart surface;
    calculating a metric representative of the surface curvature,
    wherein computing further comprises computing the principal curvatures at each point,
    wherein the metric is based upon both of the principal curvatures, and
    wherein calculating further comprises calculating the difference of principal curvatures at a point.

12. The method of claim 11, wherein calculating further comprises calculating the quotient of principal curvatures at a point.

13. The method of claim 11, further comprising displaying the three dimensional heart surface including representations of metrics.

14. The method of claim 11, wherein the metrics are displayed on the heart surface by colors.

15. The method of claim 11, further comprising selecting a region of the surface for which one or more metrics will be calculated.

* * * * *